US008501952B2

(12) United States Patent
Herzog et al.

(10) Patent No.: US 8,501,952 B2
(45) Date of Patent: Aug. 6, 2013

(54) FLUOROALKYL SILANES

(75) Inventors: Axel Hans-Joachim Herzog, West Chester, PA (US); Gerald Oronde Brown, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 35 days.

(21) Appl. No.: 13/242,434

(22) Filed: Sep. 23, 2011

(65) Prior Publication Data

US 2012/0022267 A1 Jan. 26, 2012

Related U.S. Application Data

(62) Division of application No. 12/323,593, filed on Nov. 26, 2008, now Pat. No. 8,058,463.

(60) Provisional application No. 61/005,444, filed on Dec. 4, 2007.

(51) Int. Cl.
C07D 231/00 (2006.01)
(52) U.S. Cl.
USPC ............................ 548/110; 556/421; 556/420
(58) Field of Classification Search
USPC .................. 548/110; 556/421, 420
See application file for complete search history.

(56) References Cited

U.S. PATENT DOCUMENTS

| 3,420,793 | A | 1/1969 | Pittman et al. |
|---|---|---|---|
| 3,450,738 | A | 6/1969 | Blochl et al. |
| 3,639,156 | A | 2/1972 | Pittman et al. |
| 3,646,085 | A | 2/1972 | Bartlett |
| 3,666,538 | A | 5/1972 | Domba |
| 3,787,467 | A | 1/1974 | Lucking et al. |
| 3,798,251 | A | 3/1974 | Meiller |
| 3,903,123 | A | 9/1975 | Deiner et al. |
| 4,070,152 | A | 1/1978 | Pentz |
| 4,171,282 | A | 10/1979 | Mueller |
| 4,296,034 | A | 10/1981 | Bouvet et al. |
| 4,927,950 | A | 5/1990 | Hisamoto et al. |
| 5,284,707 | A | 2/1994 | Ogawa et al. |
| 5,426,205 | A | 6/1995 | Kirchmeyer et al. |
| 5,494,949 | A | 2/1996 | Kinkel et al. |
| 6,002,038 | A | 12/1999 | Philippe et al. |
| 6,709,504 | B2 | 3/2004 | Iwato et al. |
| 6,977,307 | B2 | 12/2005 | Dams |
| 7,745,653 | B2 * | 6/2010 | Iyer et al. ............. 556/400 |
| 2005/0054804 | A1 | 3/2005 | Dams et al. |
| 2005/0121644 | A1 | 6/2005 | Dams et al. |
| 2005/0136264 | A1 | 6/2005 | Dams et al. |
| 2006/0132539 | A1 | 6/2006 | Hino et al. |
| 2006/0147645 | A1 | 7/2006 | Dams et al. |
| 2006/0159849 | A1 | 7/2006 | Morita et al. |
| 2007/0085877 | A1 | 4/2007 | Ohkuma et al. |
| 2009/0075096 | A1 | 3/2009 | Butikofer et al. |
| 2010/0038702 | A1 | 2/2010 | Oh et al. |

FOREIGN PATENT DOCUMENTS

| DE | 10051182 A1 | 5/2002 |
|---|---|---|
| EP | 0157218 A1 | 9/1988 |
| EP | 0864622 A2 | 9/1998 |
| EP | 0953331 A2 | 3/1999 |
| GB | 1140072 | 1/1969 |
| GB | 1267224 | 3/1972 |
| GB | 1298291 | 11/1972 |
| JP | 2169067 A | 6/1990 |
| JP | 10-245783 | 9/1998 |
| JP | 2000063797 A | 2/2000 |
| JP | 2002053805 A | 9/2002 |
| JP | 2006254400 A | 9/2006 |
| JP | 2007070524 A | 3/2007 |
| KR | 200050102470 A | 10/2005 |
| WO | 8606073 A1 | 10/1986 |
| WO | 0034408 A1 | 6/2000 |
| WO | 03/014131 A1 | 2/2003 |
| WO | 2007048745 A1 | 5/2007 |

OTHER PUBLICATIONS

Tesoro et al. CAS: 79: 20250, 1973.*
Meiners et al. CAS: 138: 189464, 2003.*
J. Brommelaer, Synthèse de nouveaux silanes F-alkyes dèrivès de tensioactifs non-ioniues F-alkyes,*Journal of Fluorine Chemistry*, (1991), vol. 55, pp. 79-83, Elsevier Sequoia, Lausanne, FR.
John W. Bovenkamp, *Fluoroalkyl-Substituted Siloxanes as Liquid Repellent Fabric Finishes*, Ind. Eng. Chem. P rod. Res. Dev., 1981, vol. 20, pp. 130-133, Pub. 1981 American Chemical Society.
R. J. Goos, *Effect of Ammonium Sulfate Pretreatment on Ammonia Volatilization After Urea Fertilization*, Commun. Soil Sci. Plant Anal., 30(9&10), 1325-1336 (1999), www.dekker.com.
Karl-Heinz Haas, *Functionalized coating materials based on inorganic-organic polymers*, 1999 Elsevier Science S.A., Thin Solid Films 351 (1999) 198-203.
John Howarter, *Fluorinated Surfactants as Stimuli-Responsive Polymers and Brushes*, Polymer Preprints 2005, 46(2), 21, School of Materials Engineering, Purdue University, IN.
Atsushi Hozumi, *Effect of hydrolysis groups in fluoro-alkyl silanes on water repellency of transparent two-layer hard-coatings*, Applied Surface Science 103 (1996)431-441, Elsevier Science B.V.

(Continued)

*Primary Examiner* — Rei-tsang Shiao

(57) ABSTRACT

The present invention is directed to a fluorosilane represented by $(L)_3-Si-(CH_2)_n-N(-Q^3-R_f)-Q^1-R_f$, where each n is independently an integer from 1 to 12; L is independently chosen from a hydrolysable or non-hydrolysable monovalent group $R_f$ is chosen from a $C_2-C_{12}$ perfluoroalkyl provided that: i) one fluorine atom of the perfluoroalkyl can be optionally replaced by hydrogen, and/or ii) the perfluoroalkyl can be optionally interrupted by at least one oxygen, methylene, or ethylene; $Q^1$ is chosen from the group consisting of a $C_2-C_{12}$ hydrocarbylene optionally interrupted by at least one divalent organic group; $X^1$ is chosen from O or S; and b) $Q^1$ and $Q^3$ are independently chosen from the group consisting of a $C_2-C_{12}$ hydrocarbylene interrupted by at least one of —C(O)—O— or —O—C(O)—, and optionally further interrupted by at least one divalent organic group.

4 Claims, No Drawings

OTHER PUBLICATIONS

Kenichi Izawa, *Growth process of polymer aggregates formed by perfluorooctyltriethoxysilane. Time-resolved near-IR and two-dimensional near-IR correlation studies*, Colloid Polym Sci 280; 380-388 (2002), Springer-Verlag 2002.

Peter M. Jenkins, *Thermoselective phase property of silica tethered with fluorinated chains for controlled 'release' and 'capture' of catalytic fluorous tin species*, Science Direct, Catalysis Communications 4 (2003)45-50, www.sciencedirect.com, 2002 Elsevier Science B.V.

Lou, Xia, *Study on the preparation and hydrolysis of αH, αH, ωH-perfluoroalkoxypropylmethyidichlorosilane*, Dep. Chem., Wuhan Univ., Wuhan, Peop. Rep. China, Gaofenzi Xuebao (1987), (3), 226-9, Journal.

Hui Shao, *Synthesis and surface antimicrobial activity of a novel perfluorooctylated quaternary ammonium silane coupling agent*, Science Direct, Journal of Fluorine Chemistry 125 (2004) 721-724, www.sciencedirect.com.

\* cited by examiner

FLUOROALKYL SILANES

BACKGROUND OF THE INVENTION

Fluoroalkyl silanes are a class of compounds useful for various industrial purposes. For example, fluoroalkyl silanes which have hydrolysable groups (called hydrolysable fluoroalkyl silanes), are compounds useful as surface treatment agents which provide durable hydrophobic and oleophobic coatings. In general, hydrolysable fluoroalkyl silanes can be represented with the following formula: $(RO—)_3Si—R_T$ wherein R is H or an alkyl; and $R_T$ is a monovalent organic compound terminated by a perfluoroalkyl group. When used to coat a surface, the $(RO—)_3$ moiety reacts (via hydrolysis) with various chemical groups of the surface (e.g. hydroxyl, amine, or other reactive groups) thereby bonding the fluoroalkyl silane to the surface The $R_T$ moiety comprises a divalent organic linking group which links the silicon atom to a terminal group rich in fluorine atoms whose unique electronic properties impart desirable hydrophobic and oleophobic properties in a surface coating.

Efforts have been made to engineer fluoroalkyl silanes by incorporating $R_T$ moieties which have different divalent organic linking groups which link to the silicon atom of the fluoroalkyl silane. Examples of such divalent organic linking groups include esters, sulfonamides, amides, ethers, thioethers, arylenes, urethanes, and hydrines as discussed by EP 0157218 A1; JP 2002053805 A; EP 0950662 A1; EP 0640611 A1; US 2006147645 A1; US 2005136264 A1; EP 864622 A2 as well as Bommelaer, J. et al. *J. Fluorine Chem.* 1991, 55(1), 79-83; Bovenkamp, J. W. et al. *Ind. Eng. Chem. Prod. Res. Dev.* 1981, 20(1), 130-133; Howarter, J. et al. *Polym. Preprints* (American Chemical Society, Division of Polymer Chemistry) 2005, 46(2), 21-22). The foregoing references are evidence that modification of the $R_T$ moiety is useful in the engineering of fluoroalkyl silanes. The present invention provides for fluoroalkyl silanes having $R_T$ moieties which have not been heretofore considered.

BRIEF SUMMARY OF THE INVENTION

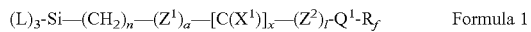

Formula 1 wherein:
each n is independently an integer from 1 to 12;

a, x, and l are integers chosen such that the moiety of Formula 1 represented by $—(Z^1)_a—[C(X^1)]_x—(Z^2)_l—$ further represents at least one of the following moieties:

i) a first moiety wherein a=1, x=1, and l=1; and
ii) a second moiety wherein a=1, x=0; and l=0;

L is independently chosen from a hydrolysable or non-hydrolysable monovalent group $R_f$ is chosen from a $C_2$-$C_{12}$ perfluoroalkyl provided that: i) one fluorine atom of the perfluoroalkyl can be optionally replaced by hydrogen, and/or ii) the perfluoroalkyl can be optionally interrupted by at least one oxygen, methylene, or ethylene; Q is chosen from the group consisting of a $C_2$-$C_{12}$ hydrocarbylene optionally interrupted by at least one divalent organic group;

$Q^1$ is chosen from the group consisting of a $C_2$-$C_{12}$ hydrocarbylene optionally interrupted by at least one divalent organic group;

$X^1$ is chosen from O or S;

the first moiety further defined wherein $Z^1$ and $Z^2$ are chosen such that:

a) $Z^1$ is —NH— and $Z^2$ is from the group consisting of —NH—, —O—, —S—, —NH—S(O)$_2$—, —N[C(O)H]—, —[HC(COOH)(R$^1$)]CH—S—, and —(R$^1$)CH—[HC(COOH)]—S—;
b) alternatively, $Z^2$ is —NH— and $Z^1$ is from the group consisting of —O—, and —S—;
c) when $Z^1$ or $Z^2$ is O, $Q^1$ is interrupted by at least one divalent moiety chosen from the group consisting of —S—, —S(O)—, —S(O)$_2$—, —NR$^1$—S(O)$_2$—, —N(CH)$_3$S(O)$_2$—, and

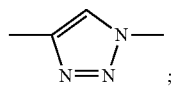

d) each $R^1$ is independently chosen from hydrogen, phenyl, or a monovalent $C_1$-$C_8$ alkyl optionally terminated by —C$_6$H$_5$, preferably H or CH$_3$;

the second moiety further defined wherein:
a) $Z^1$ is —N(-Q$^3$-R$_f$); and
b) $Q^1$ and $Q^3$ are independently chosen from the group consisting of a $C_2$-$C_{12}$ hydrocarbylene interrupted by at least one of —C(O)—O— or —O—C(O)—, and optionally further interrupted by at least one divalent organic group.

Unless otherwise stated herein the definitions used herein for L, n, $Z^1$, $X^1$, $Z^2$, $Q^1$, $Q^3$, $R^1$, and $R_f$ are identical to the definitions set forth above for Formula 1.

A preferred fluorosilane of Formula 1 is an isocyanate derived fluorosilane being a urea or thiourea fluorosilane wherein:

$Z^1$ and $Z^2$ are both —NH—;
said urea or thiourea represented by the formula:

wherein:
$X^1$ is O to form a urea fluorosilane, or $X^1$ is S to form a thiourea fluorosilane; and $Q^1$ is independently chosen from the group consisting of a $C_2$-$C_{12}$ hydrocarbylene optionally interrupted by at least one divalent moiety chosen from the group consisting of —S—, —S(O)—, —S(O)$_2$—, and —O—C(O)—NH —.

A preferred urea or thiourea fluorosilane is one wherein $R_f$ is chosen from a $C_2$-$C_{12}$ perfluoroalkyl and $Q^1$ is independently chosen from the group consisting of a $C_2$-$C_{12}$ hydrocarbylene interrupted by at least one divalent moiety chosen from the group consisting of —S—, —S(O)—, —S(O)$_2$—, and —O—C(O)—NH—.

A preferred urea or thiourea fluorosilane is one wherein $R_f$ is chosen from a $C_2$-$C_{12}$ perfluoroalkyl provided that: i) one fluorine atom of the perfluoroalkyl is replaced by hydrogen, and/or ii) the perfluoroalkyl is interrupted by at least one oxygen, methylene, or ethylene; Q is chosen from the group consisting of a $C_2$-$C_{12}$ hydrocarbylene optionally interrupted by at least one divalent organic group.

Another preferred isocyanate derived fluorosilane of Formula 1 is a carbamate fluorosilane wherein:

$Z^1$ is —NH— and $Z^2$ is —O—, or $Z^1$ is —O— and $Z^2$ is —NH—; and $X^1$ is O;

said carbamate represented by the formulae:

or

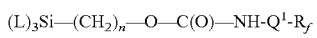

wherein:
$Q^1$ is a $C_2$-$C_{12}$ hydrocarbylene interrupted by at least one divalent moiety chosen from the group consisting of —NH—C(O)—NH—, —NH—C(S)—NH—, —S—, —S(O)—, —S(O)$_2$—, —(R$^1$)N—S(O)$_2$—,

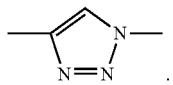

A preferred carbamate fluorosilane is one wherein $R_f$ is chosen from a $C_2$-$C_{12}$ perfluoroalkyl and $Q^1$ is independently chosen from the group consisting of a $C_2$-$C_{12}$ hydrocarbylene interrupted by at least one divalent moiety chosen from the group consisting of —S—, —S(O)—, —S(O)$_2$—, and —O—C(O)—NH—.

A preferred carbamate fluorosilane is one wherein $R_f$ is chosen from a $C_2$-$C_{12}$ perfluoroalkyl provided that: i) one fluorine atom of the perfluoroalkyl is replaced by hydrogen, and/or ii) the perfluoroalkyl is interrupted by at least one oxygen, methylene, or ethylene; Q is chosen from the group consisting of a $C_2$-$C_{12}$ hydrocarbylene optionally interrupted by at least one divalent organic group.

Another preferred isocyanate derived fluorosilane of Formula 1 is a thiolcarbamate fluorosilane wherein:
$Z^1$ is —NH— and $Z^2$ is —S—, or $Z^1$ is —S— and $Z^2$ is —NH—; and
$X^1$ is O;
said carbamate represented by the formulae:

or

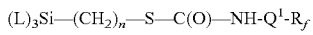

wherein:
$Q^1$ is independently chosen from the group consisting of a $C_2$-$C_{12}$ hydrocarbylene optionally interrupted by at least one divalent moiety chosen from the group consisting of —S—, —S(O)—, —S(O)$_2$—, —N(R$^1$)—C(O)—, —C(O)—N(R$^1$)—, —(R$^1$)N—S(O)$_2$—, and

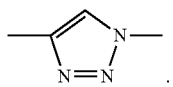

A preferred thiolcarbamate fluorosilane is one wherein $R_f$ is chosen from a $C_2$-$C_{12}$ perfluoroalkyl and $Q^1$ is independently chosen from the group consisting of a $C_2$-$C_{12}$ hydrocarbylene interrupted by at least one divalent moiety chosen from the group consisting of —S—, —S(O)—, —S(O)$_2$—, and —O—C(O)—NH—.

A preferred thiolcarbamate fluorosilane is one wherein $R_f$ is chosen from a $C_2$-$C_{12}$ perfluoroalkyl provided that: i) one fluorine atom of the perfluoroalkyl is replaced by hydrogen, and/or ii) the perfluoroalkyl is interrupted by at least one oxygen, methylene, or ethylene; Q is chosen from the group consisting of a $C_2$-$C_{12}$ hydrocarbylene optionally interrupted by at least one divalent organic group.

Another preferred isocyanate derived fluorosilane of Formula 1 is a N-sulfone urea fluorosilane wherein:
$Z^1$ is —NH—, and $Z^2$ is —NH—S(O)$_2$—; and
$X^1$ is O;
said N-sulfone urea represented by the formula:

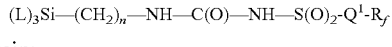

wherein:
$Q^1$ is independently chosen from the group consisting of an uninterrupted $C_2$-$C_{12}$ hydrocarbylene.

Another preferred isocyanate derived fluorosilane of Formula 1 is a formyl urea fluorosilane wherein:
a=1, x=1, and l=1; and
$Z^1$ is —NH—, and $Z^2$ is —N[C(O)H]—;
said formyl urea represented by the formula:

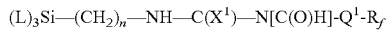

wherein:
$Q^1$ is independently chosen from the group consisting of a $C_2$-$C_{12}$ hydrocarbylene interrupted by at least one divalent moiety chosen from the group consisting of —S— and —NH—.

Another preferred fluorosilane of Formula 1 is a thioether succinamic acid fluorosilane wherein:
a=1, x=1, and l=1;
$Z^1$ is —NH— and $Z^2$ is —[HC(COOH)(R$^1$)]CH—S— or —(R$^1$)CH—[HC(COOH)]—S—;
$X^1$ is O; and $Q^1$ is —(CH$_2$)$_2$—
said thioether succinamic acid represented by the formulae:

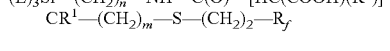

or

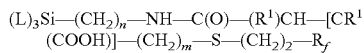

wherein m 1 or 0, pref 0, wherein each $R^1$ is indepently chosen from methyl or hydrogen preferably H.

Another preferred fluorosilane of Formula 1 is a tertiary amine fluorosilane wherein:
a=1, x=0; and l=0; and
$Z^1$ is —N[-Q$^3$-(R$_f$)]—;
said tertiary amine represented by the formula:

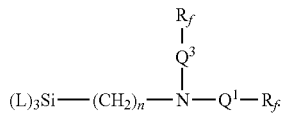

$Q^1$ and $Q^3$ is independently chosen from the group consisting of a $C_2$-$C_{12}$ hydrocarbylene interrupted by at least one —C(O)—O— and optionally further interrupted by at least one divalent moiety chosen from the group consisting of —S—, —S(O)—, —S(O)$_2$—, —N(R$^1$)—C(O)—, —C(O)—N(R$^1$)—, —(R$^1$)N—S(O)$_2$—, and

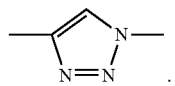

$Q^1$ and $Q^3$ are preferably the same in preferred tertiary amine fluorosilanes of the present invention,

DETAILED DESCRIPTION OF THE INVENTION

A preferred fluorosilane of Formula 1 is an isocyanate derived fluorosilane represented by $(L)_3$—Si—$(CH_2)_n$—$Z^1$—$C(X^1)$—$Z^2$-$Q^1$-$R_f$ wherein $Z^1$ is —NH— and $Z^2$ is from the group consisting of —NH—, —O—, —S—, and —NH—S$(O)_2$—; alternatively, $Z^2$ is —NH— and $Z^1$ is from the group consisting of —O—, and —S—; provided that one or both of $Z^1$ and $Z^2$ is —NH—; and provided that when $Z^1$ or $Z^2$ is —O—, $Q^1$ is a $C_2$-$C_{12}$ hydrocarbylene interrupted by at least one divalent moiety chosen from the group consisting of —S—, —S(O)—, —S(O)$_2$—, —NH—S(O)$_2$—, —N(CH$_3$)S(O)$_2$—, and

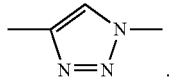

Isocyanate derived fluorosilanes of the invention can be made by reacting an isocyanate or isothiocyanate with any one of an amine, an alcohol or thiol. For example, an isocyanate terminated silane or isothiocyanate, as represented by $(L)_3$-Si—$(CH_2)_n$—N=C=$X^1$, can be reacted with a fluoroalkyl terminated by amine, alcohol, thiol, or sulfonamine, as represented by $HZ^2$-$Q^1$-$R_f$ (wherein $Z^2$ is —NH—, —O—, —S—, or —NH—S(O)$_2$—). Conversely, a silane terminated by amine, alcohol, thiol, or sulfonamine, as represented by $(L)_3$-Si—$(CH_2)_n$—$Z^1H$ (wherein $Z^1$ is —NH—, O, or S), can be reacted with a fluoroalkyl terminated by isocyanate or isothiocyanate, as represented by $X^1$=C=N-$Q^1$-$R_f$.

A preferred isocyanate derived fluorosilane is a urea fluorosilane wherein $X^1$ is O; and $Z^1$ and $Z^2$ are both —NH—; said urea fluorosilane represented by $(L)_3$Si—$(CH_2)_n$—NH—C(O)—NH-$Q^1$-$R_f$. Urea fluorosilanes of the invention can be made by reacting an isocyanate with an amine. For example, an isocyanate terminated silane, as represented by $(L)_3$-Si—$(CH_2)_n$—N=C=O, can be reacted with an amine terminated fluoroalkyl, as represented by $H_2$N-$Q^1$-$R_f$. Conversely, an amine terminated silane, as represented by $(L)_3$-Si—$(CH_2)_n$—$NH_2$, can be reacted with an isocyanate terminated fluoroalkyl, as represented by O=C=N-$Q^1$-$R_f$.

Another preferred isocyanate derived fluorosilane is a thiourea fluorosilane wherein $X^1$ is S; and $Z^1$ and $Z^2$ are both —NH—; said thiourea fluorosilane represented by $(L)_3$Si—$(CH_2)_n$—NH—C(S)—NH-$Q^1$-$R_f$. Thiourea fluorosilanes of the invention can be made by reacting an isothiocyanate with an amine. For example, a isothiocyanate terminated silane, as represented by $(L)_3$-Si—$(CH_2)_n$—N=C=S [Synthesis see eg U.S. Pat. No. 5,616,762] can be reacted with an amine terminated fluoroalkyl, as represented by $H_2$N-$Q^1$-$R_f$. Conversely, an amine terminated silane, as represented by $(L)_3$-Si—$(CH_2)_n$—$NH_2$, can be reacted with a isothiocyanate terminated fluoroalkyl, as represented by S=C=N-$Q^1$-$R_f$.

Another preferred isocyanate derived fluorosilane is a carbamate fluorosilane wherein $X^1$ is O; and $Z^1$ is —NH— and $Z^2$ is —O—, or $Z^1$ is —O— and $Z^2$ is —NH—; said carbamate fluorosilane represented by the formulae: $(L)_3$Si—$(CH_2)_n$—NH—C(O)—O-$Q^1$-$R_f$ or $(L)_3$Si—$(CH_2)_n$—O—C(O)—NH-$Q^1$-$R_f$. Carbamate fluorosilanes of the invention can be made by reacting an isocyanate with an alcohol in the presence of a catalyst such as dibutyltin dilaurate, iron tricholide, or tetraethoxy titanium. For example, an isocyanate terminated silane, as represented by $(L)_3$-Si—$(CH_2)_n$—N=C=O, can be reacted with an alcohol terminated fluoroalkyl, as represented by HO-$Q^1$-$R_f$. Conversely, an alcohol terminated silane, as represented by $(L)_3$-Si—$(CH_2)_n$—OH, can be reacted with an isocyanate terminated fluoroalkyl, as represented by O=C=N-$Q^1$-$R_f$.

The carbamate fluorosilanes of the present invention are made such that $Q^1$ is chosen from the group consisting of a $C_2$-$C_{12}$ hydrocarbylene interrupted by at least one divalent moiety chosen from the group consisting of —NH—C(O)—NH—, —NH—C(S)—NH—, —S—, —S(O)—, —S(O)$_2$—, —($R^1$)N—S(O)$_2$—,

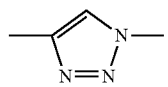

Preferably, carbamate fluorosilanes of the invention are made by reacting an isocyanate terminated silane, as represented by HO-$Q^1$-$R_f$, with an alcohol terminated fluoroalkyl chosen from the group of sulfonamindo alcohols and alcohol terminated triazoles. Preferred sulfonamido alcohols include those represented by: HO—$(CH_2)_t$—HN—S(O)$_2$—$(CH_2)_t$—$R_f$, HO—$(CH_2)_t$—N(CH$_3$)—S(O)$_2$—$(CH_2)_t$—$R_f$, HO—$(CH_2)_t$—(CH$_3$—CH$_2$—)N—S(O)$_2$—$(CH_2)_t$—$R_f$ and HO—$(CH_2)_t$—(CH$_3$—CH$_2$—CH$_2$—)N—$(CH_2)_t$—$R_f$; wherein t is independently 1, 2, or 3. Preferred alcohol terminated triazoles include those represented by

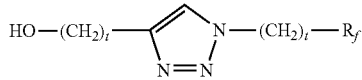

wherein t is independently 1, 2, or 3.

Another preferred isocyanate derived fluorosilane is a thiolcarbamate fluorosilane wherein $X^1$ is O; and $Z^1$ is —NH— and $Z^2$ is —S—, or $Z^1$ is —S— and $Z^2$ is —NH—; said thiolcarbamate fluorosilane represented by the formulae: $(L)_3$Si—$(CH_2)_n$—NH—C(O)—S-$Q^1$-$R_f$ or $(L)_3$Si—$(CH_2)_n$—S—C(O)—NH-$Q^1$-$R_f$. Thiolcarbamate fluorosilanes of the invention can be made by reacting an isocyanate with a thiol in the presence of a catalyst such as dibutyltin dilaurate, iron tricholide, or tetraethoxytitanium. For example, an isocyanate terminated silane, as represented by $(L)_3$-Si—$(CH_2)_n$—N=C=O, can be reacted with a thiol terminated fluoroalkyl, as represented by HS-$Q^1$-$R_f$. Conversely, a thiol terminated silane, as represented by $(L)_3$-Si—$(CH_2)_n$—SH, can be reacted with an isocyanate terminated fluoroalkyl, as represented by O=C=N-$Q^1$-$R_f$.

Another preferred isocyanate derived fluorosilane is a N-sulfone urea fluorosilane represented by $(L)_3$Si—$(CH_2)_n$—NH—C(O)—NH—S(O)$_2$-$Q^1$—$R_f$ wherein $Q^1$ is independently chosen from the group consisting of an uninterrupted $C_2$-$C_{12}$ hydrocarbylene. N-sulfone urea fluorosilanes of the invention can be made by reacting an isocyanate terminated silane, as represented by $(L)_3$-Si—$(CH_2)_n$—N=C=O, with a sulfonamine terminated fluoroalkyl, as represented by $NH_2$—S(O)$_2$-$Q^1$-$R_f$.

Another preferred isocyanate derived fluorosilane is a formyl urea fluorosilane represented by $(L)_3$Si—$(CH_2)_n$—NH—C($X^1$)—N[C(O)H]-$Q^1$-$R_f$, wherein $Q^1$ is a $C_2$-$C_{12}$ hydrocarbylene interrupted by at least one divalent moiety chosen from the group consisting of —S— and —NH—.

Isocyanate derived fluorosilanes of the invention can be made by reacting a silane terminated isocyanate, represented by $(L)_3$-Si—$(CH_2)_n$—N=C=O, with an N-vinylformamide fluoroalkyl, represented by HN[C(O)H]-$Q^1$-$R_f$, in the presence of a catalyst such as dibutyltin dilaurate, iron trichloride, or tetraethoxy titanium.

Another preferred fluorosilane of Formula 1 is a thioether succinamic acid fluorosilane represented by the formulae:

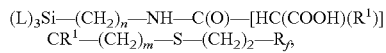

or

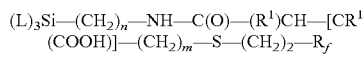

wherein m 1 or 0, pref 0; wherein each $R^1$ is indepently chosen from methyl or hydrogen preferably H. Thioether succinamic acid fluorosilanes of the invention can be made by reacting an amine terminated silane, as represented by $(L)_3$-Si—$(C_2)_n$—$NH_2$, with a succinic anhydride terminated fluoroalkyl, as represented by

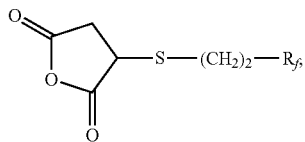

thereby yielding an isomeric mixture of thioether succinamic acid fluorosilanes represented by the formulae above.

Tertiary amine fluorosilane of the invention represented by the formula

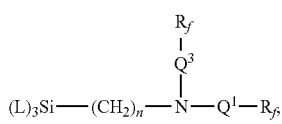

can be made by the Michael reaction of about one molar equivalent of an amino silane represented by $(L)_3Si$—$(CH_2)_n$—$NH_2$ with about two molar equivalents of a vinyl terminated fluoroalkyl selected from $Q^6$-$R_f$ or $Q^7$-$R_f$ or a mixture thereof wherein $Q^6$ and $Q^7$ are independently selected from $C_4$-$C_{10}$ hydrocarbylene terminated with propenoyloxy group ($CH_2$=$CH_2$—C(O)—O—) and said hydrocarbylene optionally interrupted by at least one divalent moiety chosen from the group consisting of —S—, —S(O)—, —S(O)$_2$—, —N($R^1$)—C(O)—, —C(O)—N($R^1$)—, —($R^1$)N—S(O)$_2$—, and

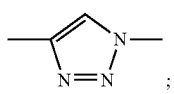

wherein $R^1$ chosen from hydrogen, phenyl, or a monovalent $C_1$-$C_8$ alkyl optionally terminated by —$C_6H_5$, preferably H or $CH_3$. One example of $Q^6$-$R_f$ or $Q^7$-$R_f$ is $CH_2$=$CH_2$—C(O)—O—$(CH_2)_2$—$R_f$. The conditions of Michael reaction are well known in the art and, in accordance with the invention, can involve a solvent such as ethanol and stirring at elevated temperatures (e.g. about 60° C.) for an extended period of time (e.g. about 5 hours).

EXAMPLES

The term "CAS#" refers to unique numerical identifiers for chemical compounds which are published by Chemical Abstracts Service of Columbus, Ohio, USA.

Example 1 synthesis of urea fluorosilane (1-[2-(3,3,4,4,5,5,6,6,7,7,8,8,8-tridecafluoro-octylsulfanyl)-ethyl]-3-(tri-ethoxysilyl-propyl)-urea)

A urea fluorosilane was synthesized by reacting an amine terminated silane (aminopropyl triethoxysilane, APTES, CAS#919-30-2) with an isocyanate terminated fluoroalkyl, 1,1,1,2,2,3,3,4,4,5,5,6,6-tridecafluoro-8-(2-isocyanato-ethylsulfanyl)-octane, as depicted by the following:

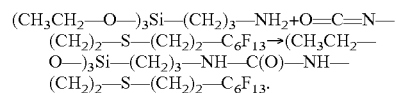

An equivalent of 1,1,1,2,2,3,3,4,4,5,5,6,6-tridecafluoro-8-(2-isocyanato-ethylsulfanyl)-octane, dissolved in toluene, was added dropwise to a solution of one equivalent of APTES, dissolved in toluene, at 0° C. The mixture was stirred at ambient temperature for one hour. The solvent was removed under vacuum to provide the desired silane as an amber oil.

$^1$H NMR (CDCl$_3$): 0.57 (m, 2H, CH$_2$Si), 1.12 (t, 9H, CH$_3$), 1.53 (m, 2H, CH$_2$CH$_2$Si), 2.31 (m, 2H, CF$_2$CH$_2$), 2.64 (m, 2H, SCH$_2$), 2.69 (m, 2H, CH$_2$S), 3.08 (m, 2H, NHCH$_2$), 3.32 (m, 2H, CH$_2$NH), 3.76 (m, 6H, OCH$_2$), 5.26 (m, 1H, NHCH$_2$), 5.45 (m, 1H, CH$_2$NH).

$^{13}$C NMR (CDCl$_3$): 8.1 (s, CH$_2$Si), 18.5 (s, CH$_3$), 22.8 (s, CH$_2$CH$_2$Si), 23.9 (s, CH$_2$S), 32.3 (m, CF$_2$CH$_2$), 33.4 (s, SCH$_2$), 40.0 (s, NHCH$_2$), 42.9 (s, CH$_2$NH), 58.7 (s, OCH$_2$), 106-122 (m, CF$_2$ and CF$_3$), 159.0 (s, CO).

The isocyanate terminated fluoroalkyl in this example was made according to the following procedure. A solution of one equivalent of 2-(3,3,4,4,5,5,6,6,7,7,8,8,8-tridecafluoro-octylsulfanyl)-ethylamine (0.1 mol) and one equivalent of triethyl amine (0.1 mol) in dry toluene (350 mL) is cooled to 0° C. (ice bath). Ethyl chloroformate (0.11 mol) is added dropwise within 20 min. The mixture, while stirring, was allowed to warm to room temperature. A second equivalent of triethyl amine (0.1 mol) is added followed by the dropwise addition of methyl trichlorosilane (0.12 mol) at 30-40° C. (addition time about 20-30 min). The mixture was then heated to 100° C. for 1 hour. After the mixture had cooled to ambient temperature the precipitated ammonium salts were filtered off. Under steady N$_2$ flow, both toluene and generated ethoxy methyl dichlorosilane were distilled off at 200 mm Hg. The residue was dried in vacuum to furnish the tile compound in 95% yield as a light red-brown liquid.

2-(3,3,4,4,5,5,6,6,7,7,8,8,8-tridecafluoro-octylsulfanyl)-ethylamine was made by the acid catalyzed deacylation of N-[2-(3,3,4,4,5,5,6,6,7,7,8,8,8-tridecafluoro-octylsulfanyl)-ethyl]-acetamide which was made by reacting 3,3,4,4,5,5,6,6,7,7,8,8,8-tridecafluoro-octane-1-thiol with N-vinylamide.

Example 2

Synthesis of Urea Fluorosilane

A urea fluorosilane was synthesized by reacting an isocyanate terminated silane (3-isocyanatopropyl triethoxysilane)

with an amine terminated fluoroalkyl, 2-(3,3,4,4,5,5,6,6,7,7,8,8,8-tridecafluoro-octylsulfanyl)-ethylamine, as depicted by the following:

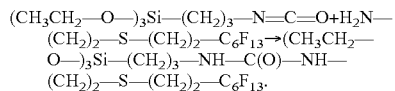

An equivalent of 2-(3,3,4,4,5,5,6,6,7,7,8,8,8-tridecafluoro-octylsulfanyl)-ethylamine, dissolved in toluene, was added dropwise to a solution of one equivalent of 3-isocyanatopropyl triethoxysilane (CAS#24801-88-5, Gelest Inc, Morrisville, Pa. 19067) dissolved in toluene, at 0° C. The mixture was stirred at ambient temperature for one hour. The solvent was removed under vacuum to provide the desired silane as an amber oil.

$^1$H NMR (CDCl$_3$): 0.57 (m, 2H, CH$_2$Si), 1.12 (t, 9H, CH$_3$), 1.53 (m, 2H, CH$_2$CH$_2$Si), 2.31 (m, 2H, CF$_2$CH$_2$), 2.64 (m, 2H, SCH$_2$), 2.69 (m, 2H, CH$_2$S), 3.08 (m, 2H, NHCH$_2$), 3.32 (m, 2H, CH$_2$NH), 3.76 (m, 6H, OCH$_2$), 5.26 (m, 1H, NHCH$_2$), 5.45 (m, 1H, CH$_2$NH).

$^{13}$C NMR (CDCl$_3$): 8.1 (s, CH$_2$Si), 18.5 (s, CH$_2$CH$_3$), 22.8 (s, CH$_2$CH$_2$Si), 23.9 (s, CH$_2$S), 32.3 (m, CF$_2$CH$_2$), 33.4 (s, SCH$_2$), 40.0 (s, NHCH$_2$), 42.9 (s, CH$_2$NH), 58.7 (s, OCH$_2$), 106-122 (m, CF$_2$ and CF$_3$), 159.0 (s, CO).

Example 3

Synthesis of Urea Fluorosilane (from C4 VDF Thioether Amine)

A urea fluorosilane was synthesized by reacting an isocyanate terminated silane (3-isocyanatopropyl triethoxysilane) with an amine terminated fluoroalkyl, 2-(3,3,5,5,6,6,7,7,8,8,8-undecafluoro-octylsulfanyl)-ethyl-ammonium chloride, as depicted by the following:

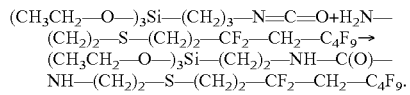

Di-i-propyl ethyl amine (one equivalent) was added dropwise to a mixture of 2-(3,3,5,5,6,6,7,7,8,8,8-undecafluoro-octylsulfanyl)-ethyl-ammonium chloride (one equivalent) and 3-isocyanatopropyl triethoxysilane (one equivalent) (CAS#24801-88-5, Gelest Inc, Morrisville, Pa. 19067) in anhydrous THF ambient temperature. The mixture was stirred at 60° C. for one hour. The solvent was removed under vacuum and the pasty residue was triturated with a mixture of toluene and hexanes (1:2) and filtered. The filtrate was dried under reduced pressure to furnish the desired silane in quantitative yield as a amber oil.

$^1$H NMR (CDCl$_3$): 0.56 (m, 2H, CH$_2$Si), 1.13 (t, 9H, CH$_3$), 1.52 (m, 2H, CH$_2$CH$_2$Si), 2.24 (m, 2H, CF$_2$CH$_2$), 2.67 (m, 4H, CH$_2$S and CF$_2$CH$_2$CF$_2$), 3.07 (m, 2H, SCH$_2$), 3.29 (m, 2H, NHCH$_2$), 3.58 (m, 2H, SCH$_2$CH$_2$NH), 3.74 (m, 6H, OCH$_2$), 5.42 (m, 1H, NHCH$_2$), 5.74 (m, 1H, CH$_2$NH).

2-(3,3,5,5,6,6,7,7,8,8,8-undecafluoro-octylsulfanyl)-ethyl-ammonium chloride was made by was made by the deacylation of N-[2-(3,3,5,5,6,6,7,7,8,8,8-udecafluoro-octylsulfanyl)-ethyl]-formamide as follows. Concentrated hydrogen chloride solution (37.5 w/% in water, five to six-fold molar excess) was added to a solution of one equivalent of Amide Intermediate #3 in ethanol at 0° C. The reaction mixture was allowed to warm to ambient temperature while being stirred. After the initial foam formation ceased the reaction mixture was stirred at 70° C. for 5 hours. The progress of the reaction was monitored via Gas Chromatography. The 2-(3,3,5,5,6,6,7,7,8,8,8-undecafluoro-octylsulfanyl)-ethyl-ammonium chloride was isolated in quantitative yield by stripping all volatiles under reduced pressure.

N-[2-(3,3,5,5,6,6,7,7,8,8,8-udecafluoro-octylsulfanyl)-ethyl]-formamide was made by reacting, 3,5,5,6,6,7,7,8,8,8-undecafluoro-octane-1-thiol with N-vinylamide.

3,5,5,6,6,7,7,8,8,8-undecafluoro-octane-1-thiol was made as follows. Under nitrogen, potassium thioacetate (1.1 equivalents) was added to a solution of 1,1,1,2,2,3,3,4,4,6,6-undecafluoro-8-iodo-octane (1 equivalent) in THF. The reaction mixture was stirred at 50° for 5 hours. The THF was removed under reduced pressure. The distillation residue was dissolved in methanol (25 mL/0.1 mol) and treated with hydrochloric acid (37 w/% in water, three fold excess). Additional degassed water was added to the mixture. 3,5,5,6,6,7,7,8,8,8-undecafluoro-octane-1-thiol was collected as the fluorous bottom layer and purified via distillation.

Example 4

Synthesis of urea fluorosilane 1-[2-(3,3,4,4-tetrafluoro-4-heptafluoropropyloxy-butylsulfanyl)-ethyl]-3-(triethoxysilyl-propyl)-urea (from PPVE thioether amine)

A urea fluorosilane was synthesized by reacting an isocyanate terminated silane (3-isocyanatopropyl triethoxysilane) with an amine terminated fluoroalkyl, 2-(3,3,4,4-tetrafluoro-4-heptafluoropropyloxy-butylsulfanyl)-ethylamine, as depicted by the following:

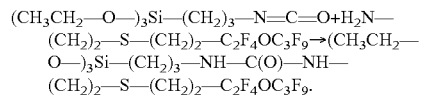

An equivalent of 2-(3,3,4,4-tetrafluoro-4-heptafluoropropyloxy-butylsulfanyl)-ethylamine was added dropwise to a solution of one equivalent of 3-isocyanatopropyl triethoxysilane. The reaction temperature rose to 65° C. due to the occurring exotherm. The reaction mixture was stirred 65° C. for one additional hour to provide the desired silane as an amber oil in quantitative yield.

$^1$H NMR (CDCl$_3$): 0.65 (m, 2H, CH$_2$Si), 1.23 (t, 9H, CH$_3$), 1.62 (m, 2H, CH$_2$CH$_2$Si), 2.31 (m, 2H, CF$_2$CH$_2$), 2.71 (m, 2H, SCH$_2$), 2.75 (m, 2H, CH$_2$S), 3.15 (m, 2H, NHCH$_2$), 3.40 (m, 2H, CH$_2$NH), 3.82 (m, 6H, OCH$_2$), 5.00 (m, 1H, NHCH$_2$), 5.17 (m, 1H, CH$_2$NH).

The amine terminated fluoroalkyl in this example 2-(3,3,4,4-tetrafluoro-4-heptafluoropropyloxy-butylsulfanyl)-ethylamine was made from the acid catalyzed deacylation of N-[2-(3,3,4,4-tetrafluoro-4-heptafluoropropyloxy-butylsulfanyl)-ethyl]-formamide which in turn was made by reacting 3,3,4,4-tetrafluoro-4-heptafluoropropyloxy-butane-1-thiol with N-vinylformamide.

Example 5

Synthesis of urea fluorosilane 3,3,4,4,5,5,6,6,7,7,8,8,8-tridecafluoro-octane-1-sulfonic acid-N-methyl-{3-[3-(triethoxysilyl-propyl)-ureido]-propyl}-amide (from C6-sulfonamido amine)

A urea fluorosilane was synthesized by reacting an isocyanate terminated silane (3-isocyanatopropyl triethoxysilane) with an amine terminated fluoroalkyl, 3,3,4,4,5,5,6,6,7,7,8,8, 8-tridecafluoro-octane-1-sulfonic acid (3-amino-propyl)-N-methyl-amide, as depicted by the following:

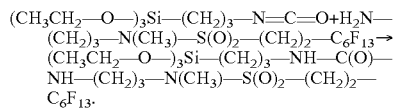

In accord to Laduron, F. et al. *Org. Proc. Res. Dev.* 2005, 9, 104-105, a flask (500 mL) equipped with a Dean-Stark trap and a condenser was charged with a mixture of the N-methyl-1,2-propanediamine (73.0 g; 0.83 mol, 88.2 g/mol) and MIBK (230 mL) to in-situ generate N-(1,3-dimethyl-butylidene)-N'-methyl-propane-1,3-diamine. The mixture was heated to reflux under nitrogen until no more water (15 mL, 0.83 mol) was produced (6 h). Triethyl amine (91 mL, 0.9 mol) was added to the MIBK solution of the ketimine. The mixture was cooled to 0° C. A toluene solution of 3,3,4,4,5,5,6,6,7,7,8,8,8-tridecafluorooctanyl-1-sulfonylchloride (529.5 g of a 70 w/% solution, 370.7 g active ingredient; 0.83 mol. Available from DuPont as Capstone™ BL67) was then added drop-wise to the flask. After stirring for 5 h at room temperature and an additional hour at 50° C. the suspension was filtered, and the solvents were removed from the filtrate under reduced pressure. The off-white solid residue was re-suspended in water (300 mL) and 2-propanol (100 mL), and the mixture was heated to 65° C. until the hydrolysis was completed (GC). Solvents were distilled off under reduced pressure providing the crude free primary amine. Recrystallization from 2:1 mixtures of ether and toluene furnished 3,3,4,4,5,5,6,6,7,7,8,8,8-tridecafluoro-octane-1-sulfonic acid (3-amino-propyl)-methyl-amide in 49% yield (202 g, 0.41 mol) with a melting point of 135° C. [$^1$H-NMR (CDCl$_3$): 1.53 (br, 2H, NH$_2$), 1.76 (m, 2H, CH$_2$CH$_2$NH$_2$), 2.63 (m, 2H, CF$_2$CH$_2$), 2.79 (m, 2H, NCH$_3$CH$_2$), 2.90 (s, 3H, NCH$_3$), 3.17 (m, 2H, CH$_2$SO$_2$N), 3.33 (m, 2H, NCH$_2$)].

One equivalent of 3,3,4,4,5,5,6,6,7,7,8,8,8-tridecafluoro-octane-1-sulfonic acid (3-amino-propyl)-N-methyl-amide, dissolved in tetrahydrofuran (THF) was added dropwise to a solution of one equivalent of 3-isocyanatopropyl triethoxysilane in THF at 0° C. The reaction mixture was allowed to warm to ambient temperature and was then stirred at 50° C. for one additional hour. The solvent was removed in vacuo to provide the desired silane as an off-white solid in quantitative yield.

$^1$H NMR (CDCl$_3$): 0.63 (m, 2H, CH$_2$Si), 1.21 (t, 9H, CH$_3$), 1.59 (m, 2H, CH$_2$CH$_2$Si), 1.78 (m, 2H, CH$_2$CH$_2$NCH$_3$), 2.59 (m, 2H, CF$_2$CH$_2$), 2.88 (s, 3H, NCH$_3$), 3.16 (m, 4H, CH$_2$NH and CH$_2$SO$_2$), 3.24 (m, 4H, NHCH$_2$ and CH$_3$NCH$_2$), 3.82 (m, 6H, OCH$_2$).

Example 6

Carbamate Fluorosilane from a Sulfonamide Alcohol (FORAFAC 1051 Alcohol)

a Carbamate Fluorosilane was Synthesized by Reacting an isocyanate terminated silane (3-isocyanatopropyl triethoxysilane) with a sulfonamido alcohol, 3,3,4,4,5,5,6,6,7,7,8,8,8-tridecafluoro-octane-1-sulfonic acid (3-hydroxy-ethyl)-methyl-amide (commercially available from DuPont as FORAFAC® 1051 alcohol) in the presence of a catalyst (dibutyltin dilaurate) according to the following reaction scheme:

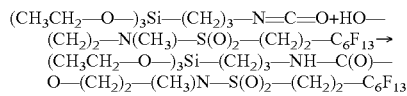

An equivalent of each, 3-isocyanatopropyl triethoxysilane and 3,3,4,4,5,5,6,6,7,7,8,8,8-tridecafluoro-octane-1-sulfonic acid (3-hydroxy-ethyl)-methyl-amide, as well as 0.02 equivalents of dibutyltin dilaurate were allowed to react in THF at 50° C. for 5 h. The solvent was removed under vacuum to provide the desired silane as an amber oil.

$^1$H NMR (CDCl$_3$): 0.54 (m, 2H, CH$_2$Si), 1.14 (t, 9H, CH$_3$), 1.55 (m, 2H, CH$_2$CH$_2$Si), 2.55 (m, 2H, CF$_2$CH$_2$), 2.91 (s, 3H, NCH$_3$), 3.10 (m, 4H, CH$_2$NH and CH$_2$SO$_2$), 3.41 (m, 2H, CH$_3$NCH$_2$), 3.73 (m, 6H, OCH$_2$), 4.15 (m, 2H, CH$_2$OCO), 5.03 (s, br, 1H, NH).

$^{13}$C NMR (CDCl$_3$): 7.8 (s, CH$_2$Si), 18.3 (s, CH$_2$CH$_3$), 23.3 (s, CH$_2$CH$_2$Si), 26.4 (m, CF$_2$CH$_2$), 35.1 (s, NCH$_3$), 42.5 (s, CH$_3$NCH$_2$), 43.6 (s, NHCH$_2$), 49.4 (s, CH$_2$SO$_2$), 58.6 (s, OCH$_2$), 61.8 (s, CH$_2$OCO), 106-122 (m, CF$_2$ and CF$_3$), 156.0 (s, CO).

Example 7 carbamate fluorosilane from a sulfonamido alcohol, [3-(triethoxysilyl)-propyl]-carbamic acid 2-(3,3,4,4,5,5,6,6,7,7,8,8,8-tridecafluoro-octane-1-sulfonylamido)-ethyl ester A carbamate fluorosilane was synthesized by reacting an isocyanate terminated silane (3-isocyanatopropyl triethoxysilane) with a sulfonamido alcohol, 3,3,4,4,5,5,6,6,7,7,8,8,8-tridecafluoro-octane-1-sulfonic acid (2-hydroxy-ethyl)-amide, in the presence of a catalyst (dibutyltin dilaurate) according to the follow reaction scheme:

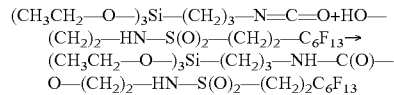

An equivalent of each, 3-isocyanatopropyl triethoxysilane and 3,3,4,4,5,5,6,6,7,7,8,8,8-tridecafluoro-octane-1-sulfonic acid (2-hydroxy-ethyl)-amide (in accordance with British Patent GB1298291A hereby incorporated by reference), as well as 0.02 equivalents of dibutyltin dilaurate were allowed to react in THF at 50° C. for 5 h. The solvent was removed under vacuum to provide the desired silane as an amber oil.

$^1$H NMR (CDCl$_3$): 0.60 (m, 2H, CH$_2$Si), 1.18 (t, 9H, CH$_3$), 1.59 (m, 2H, CH$_2$CH$_2$Si), 2.60 (m, 2H, CF$_2$CH$_2$), 3.12 (m, 2H, CH$_2$NH), 3.26 (m, 2H, CH$_2$SO$_2$), 3.36 (m, 2H, HNCH$_2$), 3.77 (m, 6H, OCH$_2$), 4.15 (m, 2H, CH$_2$OCO), 5.20 (s, br, 1H, CONH), 5.58 (s, br, 1H, SO$_2$NH).

$^{13}$C NMR (CDCl$_3$): 6.6 (s, CH$_2$Si), 17.4 (s, CH$_2$CH$_3$), 22.3 (s, CH$_2$CH$_2$Si), 24.9 (m, CF$_2$CH$_2$), 42.5 (s, SO$_2$NCH$_2$), 43.3 (s, NHCH$_2$), 45.4 (s, CH$_2$SO$_2$), 57.5 (s, OCH$_2$), 62.7 (s, CH$_2$OCO), 106-122 (m, CF$_2$ and CF$_3$), 155.5 (s, CO).

Example 8 carbamate fluorosilane from an alcohol terminated triazole, [2-(triethoxysilyl-propyl]-carbamic acid 1-(3,3,4,4,5,5,6,6,7,7,8,8,8-tridecafluoro-octyl)-1H-[1,2,3]-triazol-4-ylmethyl ester A carbamate fluorosilane was synthesized by reacting an isocyanate terminated silane (3-isocyanatopropyl triethoxysilane) with a alcohol terminated triazole, [1-(3,3,4,4,5,5,6,6,7,7,8,8,8-tridecafluoro-octyl)-1H-[1,2,3]triazol-4-yl]-methanol, in the presence of a catalyst (dibutyltin dilaurate) according to the follow reaction scheme:

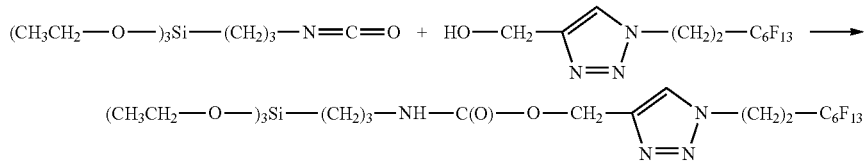

An equivalent of each, 3-isocyanatopropyl triethoxysilane and [1-(3,3,4,4,5,5,6,6,7,7,8,8,8-tridecafluoro-octyl)-1H-[1,2,3]triazol-4-yl]-methanol (E. J. Acosta et al., US Patent Application US2007066762A1, 2007) as well as 0.02 equivalents of dibutyltin dilaurate were allowed to react in THF at 50° C. for 5 h. The solvent was removed under vacuum to provide the desired silane as an amber oil in quantitative yield.

$^1$H NMR (CDCl$_3$): 0.57 (m, 2H, CH$_2$Si), 1.17 (t, 9H, CH$_3$), 1.58 (m, 2H, CH$_2$CH$_2$Si), 2.78 (m, 2H, CF$_2$CH$_2$), 3.12 (m, 2H, CH$_2$NH), 4.63 (m, 2H, CH$_2$CH$_2$N), 5.05 (s, br, 1H, CONH), 5.15 (s, 2H, CH$_2$OCO), 7.66 (NCH).

$^{13}$C NMR (CDCl$_3$): 7.9 (s, CH$_2$Si), 18.4 (s, CH$_2$CH$_3$), 23.5 (s, CH$_2$CH$_2$Si), 32.0 (m, CF$_2$CH$_2$), 42.4 (s, CH$_2$N), 43.7 (s, NHCH$_2$), 57.5 (s, CH$_2$OCO), 58.7 (s, OCH$_2$), 108-118 (m, CF$_2$ and CF$_3$), 124.5 (s, CHN), 144.4 (s, CN), 156.5 (s, CO).

Example 9 carbamate fluorosilane from ETFE-alcohol (α-fluoro-ω-2-hydroxyethyl terminated ethylene-tetrafluoroethylene co-polymer) {3-(4,4,4-triethoxysilyl-propyl)-carbamic acid-3,3,4,4,7,7,8,8,11,11,12,12,12-tridecafluoro-dodecyl ester}

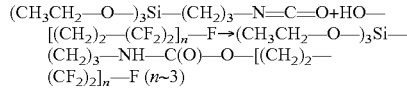

A solution of 3 3,3,4,4,7,7,8,8,11,11,12,12,12-tridecafluoro-dodecan-1-ol (average molecular weight of 420.0 g/mol, 25.0 g, 61.0 mmol), 3-isocyanato-propyl-triethoxysilane (15.1 g, 61.0 mmol) and iron trichloride (4 mg, 2.4 μmol) in anhydrous MIBK (methyl isobutyl ketone) was heated at reflux temperature for 3 h. The solvent was removed in vacuo to furnish the title silane in quantitative yield as a light yellow oil.

$^1$H NMR (CDCl$_3$): 0.64 (m, 2H, CH$_2$Si), 1.22 (t, 9H, CH$_3$), 1.63 (m, 2H, CH$_2$CH$_2$Si), 2.33 (m, 10H, CF$_2$CH$_2$), 3.18 (m, 2H, CH$_2$NH), 3.82 (q, 6H, OCH$_2$), 4.34 (m, 2H, CH$_2$OCO), 5.08 (s, br, 1H, NH).

HO—[(CH$_2$)$_2$—(CF$_2$)$_2$]$_n$—F was made according to procedures set forth in U.S. patent application Ser. No. 12/152,312 filed on May 14, 2008, hereby incorporated by reference.

Example 10 carbamate fluorosilane from C4-VDF-alcohol {3-(4,4,4-triethoxysilyl-propyl)-carbamic acid-3,3,5,5,6,6,7,7,8,8,8-undecafluoro-octyl ester}

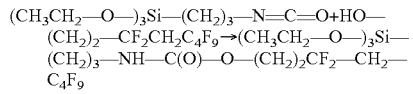

A neat mixture of 3,3,5,5,6,6,7,7,8,8,8-undecafluoro-octan-1-ol (20.0 g, 61.0 mmol) and 3-isocyanato-propyl-triethoxysilane (15.1 g, 61.0 mmol,) was heated to 60 deg C. Iron trichloride (4 mg, 2.4 μmol), dissolved in MIBK (methyl isobutyl ketone, 1 mL) was added. The reaction temperature immediately increased 110° C. After the exotherm ceased, the reaction mixture was heated to 85° C. for 3 h. A negative isocyanate test indicated completion of the reaction. The mixture was dried in vacuo to quantitatively yield the title compound as an amber oil.

$^1$H NMR (CDCl$_3$): 0.59 (m, 2H, CH$_2$Si), 1.18 (t, 9H, CH$_3$), 1.60 (m, 2H, CH$_2$CH$_2$Si), 2.34 (m, 2H, CF$_2$CH$_2$), 2.34 (m, 2H, CF$_2$CH$_2$CF$_2$), 3.15 (m, 2H, CH$_2$NH), 3.79 (q, 6H, OCH$_2$), 4.26 (m, 2H, CH$_2$OCO), 5.00 (s, br, 1H, NH).

HO—(CH$_2$)$_2$—CF$_2$—CH$_2$—C$_4$F$_9$ was synthesized according to U.S. Pat. No. 3,916,009, CIBA-GEIGY AG, 1975.

Example 11 thiolcarbamate fluorosilane [(3-(triethoxysilyl-propyl)-thiocarbamic acid S-(3,3,4,4,5,5,6,6,7,7,8,8,8-tridecafluoro-octyl) ester]

A thiolcarbamate fluorosilane was synthesized by reacting an isocyanate (3-isocyanatopropyl triethoxysilane) with a thiol (1H,1H,2H,2H-perfluorooctyl-1-thiol) in the presence of a catalyst (dibutyltin dilaurate) according to the follow reaction scheme:

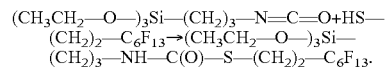

An equivalent of each, isocyanatopropyl triethoxysilane, and 1H,1H,2H,2H-perfluorooctyl-1-thiol (CAS#34451-26-8), as well as 0.02 equivalents of dibutyltin dilaurate were heated to reflux in MIBK (methyl isobutyl ketone) for 3 h. The solvent was distilled under vacuum to provide the desired silane as an amber oil.

$^1$H NMR (CDCl$_3$): 0.62 (m, 2H, CH$_2$Si), 1.22 (t, 9H, CH$_3$), 1.65 (m, 2H, CH$_2$CH$_2$Si), 2.44 (m, 2H, CF$_2$CH$_2$), 3.08 (m, 2H, CH$_2$S), 3.29 (m, 2H, CH$_2$N), 3.81 (q, 6H, OCH$_2$), 5.91 (s, br, 1H, NH).

Example 12 thiolcarbamate fluorosilane from C4 VDF thiol [3-(triethoxysilyl-propyl)-thiocarbamic acid S-(3,3,5,5,6,6,7,7,8,8,8-undecafluoro-octyl) ester]

A thiolcarbamate fluorosilane was synthesized by reacting an isocyanate (3-isocyanatopropyl triethoxysilane) with a thiol (3,3,5,5,6,6,7,7,8,8,8-undecafluoro-octane-1-thiol) in the presence of a catalyst (dibutyltin dilaurate) according to the follow reaction scheme:

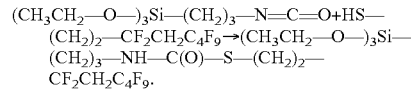

An equivalent of each, isocyanatopropyl triethoxysilane, and 3,3,5,5,6,6,7,7,8,8,8-undecafluoro-octane-1-thiol (CH3213), as well as 0.02 equivalents of dibutyltin dilaurate were heated at 70° C. for 12 h to furnish the desired silane as an amber oil in quantitative yield.

¹H NMR (CDCl₃): 0.63 (m, 2H, CH₂Si), 1.24 (t, 9H, CH₃), 1.67 (m, 2H, CH₂CH₂Si), 2.34 (m, 2H, CF₂CH₂), 2.74 (m, 2H, CF₂CH₂CF₂), 3.06 (m, 2H, CH₂S), 3.32 (m, 2H, NCH2), 3.84 (q, 6H, OCH₂), 5.93 (s, br, 1H, NH).

Example 13

N-sulfone urea fluorosilane [3,3,4,4,5,5,6,6,7,7,8,8,8-tridecafluoro-octylsulfonyl ureido-N-(3-triethoxysilyl-propane]

A N-sulfone urea fluorosilane was synthesized by reacting an isocyanate (3-isocyanatopropyl triethoxysilane) with a sulfonamide (3,3,4,4,5,5,6,6,7,7,8,8,8-tridecafluoro-octane-1-sulfonic acid amide) in the presence of a catalyst (dibutyltin dilaurate) according to the follow reaction scheme:

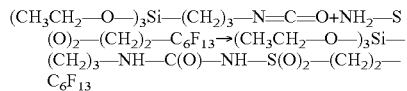

A THF solution of one equivalent of 3-isocyanatopropyl triethoxysilane and one equivalent of 3,3,4,4,5,5,6,6,7,7,8,8,8-tridecafluoro-octane-1-sulfonic acid amide (E2001100-00087, prepared according to P. Bouvet et al., DE2002460A1, 1970) and 0.02 equivalents of dibutyltin dilaurate was stirred at 65° C. for 8 h (the reaction also proceeds without the use of the catalyst under the same reaction conditions). The solvent was removed under vacuum to provide the desired silane as an off-white solid (Mp 78° C.).

¹H NMR (MeOH-d₄): 0.62 (m, 2H, CH₂Si), 1.18 (t, 9H, CH₃), 1.57 (m, 2H, CH₂CH₂Si), 2.72 (m, 2H, CF₂CH₂), 3.07 (m, 2H, CH₂N), 3.34 (m, 2H, CH₂S), 3.61 (q, 6H, OCH₂), Urea-NH not detected.

Example 14 synthesis of formyl urea fluorosilane {1-[2-(3,3,4,4,5,5,6,6,7,7,8,8,8-tridecafluoro-octylsulfanyl)-ethyl]-3-(triethoxysilyl-propyl)-12(N)-formyl-urea}

A formyl urea fluorosilane was synthesized by reacting an isocyanate terminated silane (3-isocyanatopropyl triethoxysilane) with an N-vinylformamide fluoroalkyl {N-[2-(3,3,4,4,5,5,6,6,7,7,8,8,8-tridecafluoro-octylsulfanyl)-ethyl]-formamide, in the presence of a catalyst (dibutyltin dilaurate) according to the following reaction scheme:

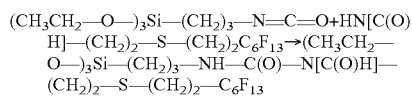

A THF (tetrahydrofuran) solution of one equivalent of 3-isocyanatopropyl triethoxysilane and one equivalent of N-[2-(3,3,4,4,5,5,6,6,7,7,8,8,8-tridecafluoro-octylsulfanyl)-ethyl]-formamide and 0.02 equivalents of dibutyltin dilaurate was stirred at 65° C. for 8 h. The solvent was removed under vacuum to provide the desired silane as an amber oil.

¹H NMR (CDCl₃): 0.61 (m, 2H, CH₂Si), 1.15 (t, 9H, CH₃), 1.66 (m, 2H, CH₂CH₂Si), 2.31 (m, 2H, CF₂CH₂), 2.68 (m, 4H, CH2 SCH₂), 3.22 (m, 2H, CH₂NCOH), 3.42 (m, 2H, NHCH₂), 6.43 (s, br, 1H, NH), 8.11 (s, 1H, COH).

N-[2-(3,3,4,4,5,5,6,6,7,7,8,8,8-tridecafluoro-octylsulfanyl)-ethyl]-formamide which was made by reacting 3,3,4,4,5,5,6,6,7,7,8,8,8-tridecafluoro-octane-1-thiol with N-vinylformamide. All volatiles were removed under reduced pressure to furnish N-[2-(3,3,4,4,5,5,6,6,7,7,8,8,8-tridecafluoro-octylsulfanyl)-ethyl]-formamide as an off-white solid.

3,3,4,4,5,5,6,6,7,7,8,8,8-tridecafluoro-octane-1-thiol which was made as follows. Under nitrogen thiourea (1.1 equivalents) and 1-iodo-2-perfluorohexylethane (1 equivalent) were added to a degassed mixture of dimethoxyethane (DME, 9 parts) and water (1 part). The reaction mixture was held at reflux temperature for 8 hours. Most of the DME was distilled off and the distillation residue was allowed to cool to ambient temperature. Under stirring a solution of sodium methoxide in methanol (1 molar, 1.1 equivalents) was added to the suspension. Degassed water was added to the mixture. 3,3,4,4,5,5,6,6,7,7,8,8,8-tridecafluoro-octane-1-thiol was collected quantitatively as the fluorous bottom layer.

Example 15

Thioether Succinamic Acid Fluorosilane

A thioether succinamic acid fluorosilane {3-(3,3,4,4,5,5,6,6,7,7,8,8,8-tridecafluoro-octylsulfanyl)-N-(3-triethoxysilyl-propyl)-succinamic acid (A) & 2-(3,3,4,4,5,5,6,6,7,7,8,8,8-tridecafluoro-octylsulfanyl)-N-(3-triethoxysilyl-propyl)-succinamic acid (B)} was made by reacting an amine terminated silane (aminopropyl triethoxysilane) with a succinic anhydride terminated fluoroalkyl {3-(3,3,4,4,5,5,6,6,7,7,8,8,8-tridecafluoro-octylsulfanyl)-dihydro-furan-2,5-dione} according to the following reaction scheme:

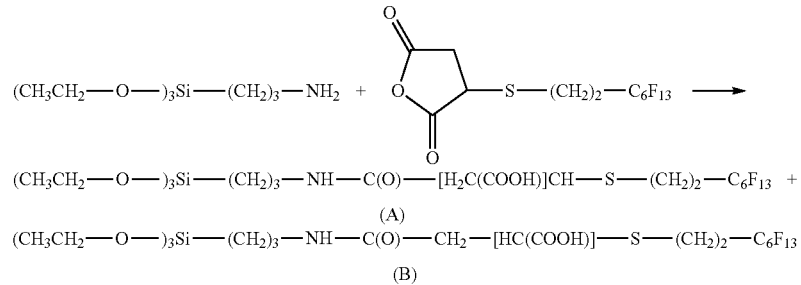

To a suspension of 3-(3,3,4,4,5,5,6,6,7,7,8,8,8-tridecafluoro-octylsulfanyl)-dihydro-furan-2,5-dione (prepared according to U.S. Pat. No. 4,171,282 hereby incorporated by reference), freshly prepared in toluene, was added one equivalent of APTES (Aminopropyl triethoxysilane, CAS#919-30-2) dissolved in toluene at 0° C. The reaction mixture was stirred at ambient temperature for 2 hours. After removal of all volatiles the desired silane was obtained as a dark-amber oil as a 2:1 mixture of the isomers A and B.

$^1$H NMR (CDCl$_3$): 0.64 (m, br, 2H, CH$_2$Si), 1.24 (t, 9H, CH$_3$), 1.63 (m, br, 2H, CH$_2$CH$_2$Si), 2.47 (m, br, 3H, CF$_2$CH$_2$ and CH$_2$COO), 2.85 and 2.92 (2×m, 2H, 2.68, CH$_2$S), 3.13 (m, 0.5H, CH$_2$COO), 3.19 (m, br, 2H, NHCH$_2$), 3.30 (m, br, 1H, CH$_2$COO), 3.52 (m, 1H, SCHCON), 3.64 (m, 1H, CH$_2$CONH), 3.82 (q, 6H, OCH$_2$), 6.43 (s, br, 1H, NH), 10.65 (s, 1H, COOH).

$^{13}$C NMR (CDCl$_3$): 7.8 (s, CH$_2$Si), 18.3 (s, CH$_2$CH$_3$), 23.4 (s, CH$_2$CH$_2$Si), 31.9 (m, CF$_2$CH$_2$), 35.7 (s, CH$_2$CONH), 39.4 and 39.8 (s, CH$_2$S), 41.4 and 42.5 (s, CH$_2$NH), 45.8 (s, SCH), 46.4 (s, SCH$_2$), 58.7 (s, OCH$_2$), 108-118 (m, CF$_2$ and CF$_3$), 171.0 and 171.8 (s, CONH), 176.1 and 176.8 (s, COOH).

Example 16

Tertiary Amine Fluorosilane from C$_6$ Acrylate

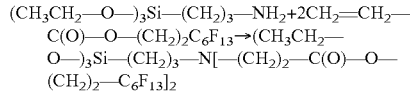

A solution of one equivalent of APTES (Aminopropyl triethoxysilane, CAS#919-30-2) and two equivalents acrylic acid 3,3,4,4,5,5,6,6,7,7,8,8,8-tridecafluoro-octyl ester (CAS#17527-29-6) in absolute ethanol were allowed to stir at 60° C. for 5 h. The solvent was distilled of under reduced pressure to provide the desired twin-tail silane (tertiary amine fluorosilane) quantitatively as an amber oil.

1H NMR (THF-d8): 0.68 (m, 2H, CH$_2$Si), 1.63 (m, 2H, CH$_2$CH$_2$Si), 2.56 (m, br, 6H, CH$_2$COO and NCH$_2$), 2.70 (m, 4H, CF$_2$CH$_2$), 2.86 (t, 4H, OOCCH$_2$CH$_2$N), 3.63 (s, 9H, OCH$_3$), 4.48 (m, 4H, CH$_2$OOC).

13C NMR (THF-d8): 7.8 (s, CH$_2$Si), 21.9 (s, CH$_2$CH$_2$Si), 31.8 (m, CF$_2$CH$_2$), 33.9 (s, CH$_2$COO), 49.7 (s, OCH$_3$), 57.3 (OOCCH$_2$CH$_2$N), 58.0 (s, NCH$_2$), 61.5 (s, CH$_2$OOC), 109-121 (m, CF$_2$ and CF$_3$), 172.8 (s, COO).

Example 17

Tertiary Amine Fluorosilane from Acrylate

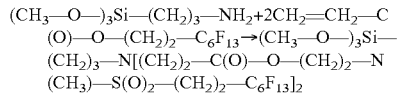

A mixture one equivalent of 3-aminopropyl trimethoxysilane (commercially available as DYNASYLAN AMMO from Evonik Degussa GmbH of Germany) and two equivalents of acrylic acid-2-[N-methyl[(3,3,4,4,5,5,6,6,7,7,8,8,8-tridecafluorooctyl)-1-sulfonylamino]-ethyl ester (prepared according to U.S. Pat. No. 5,439,998 hereby incorporated by reference) was allowed to stir at 70° C. for 5 h to provide the desired twin-tail silane quantitatively as a amber oil.

1H NMR (THF-d8): 0.67 (m, 2H, CH$_2$Si), 1.63 (m, 2H, CH$_2$CH$_2$Si), 2.54 (2×m, 6H, CH$_2$COO and NCH$_2$), 2.79 (m, 4H, CF$_2$CH$_2$), 2.86 (t, 4H, OOCCH$_2$CH$_2$N), 3.08 (s, 6H, NCH$_3$), 3.41 (m, 4H, CH$_2$SO$_2$), 3.60 (m, 4H, CH$_3$ NCH$_2$), 3.63 (s, 9H, OCH$_3$), 4.33 (m, 4H, CH$_2$OCO).

13C NMR (THF-d8): 7.7 (s, CH$_2$Si), 21.6 (s, CH$_2$CH$_2$Si), 27.0 (m, CF$_2$CH$_2$), 33.7 (s, NCH3), 36.7 (s, CH$_2$COO), 42.4 (s, OCH$_3$), 49.7 (s, CH$_3$ NCH$_2$), 50.4 (s, OOCCH$_2$CH$_2$N), 50.8 (s, CH$_2$SO$_2$), 57.7 (s, NCH$_2$C$_2$H$_4$), 62.8 (s, CH$_2$OOC), 109-121 (m, CF$_2$ and CF$_3$), 172.8 (s, COO).

Example 18

Tertiary Amine Fluorosilane from C$_4$ VDF Acrylate

A bis-fluoroalkyl (twin-tail) silane with ester and tertiary amine tether moieties was synthesized according to:

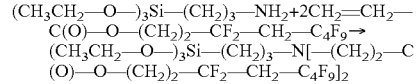

A solution of one equivalent of APTES (Aminopropyl triethoxysilane, CAS#919-30-2) and two equivalents acrylic acid 3,3,5,5,6,6,7,7,8,8,8-undecafluoro-octyl ester (synthesized according to U.S. Pat. No. 3,916,009, CIBA-GEIGY AG, 1975) in absolute ethanol were allowed to stir at 60° C. for 5 h. The solvent was distilled of under reduced pressure to provide the desired twin-tail silane (tertiary amine fluorosilane) quantitatively as a colorless oil.

1H NMR (MeOH-d4): 0.60 (m, 2H, CH$_2$Si), 1.18 (t, 9H, CH$_3$), 1.56 (m, 2H, CH$_2$CH$_2$Si), 2.47 (m, br, 10H, CF$_2$CH$_2$CH$_2$ and OOCCH2 and NCH$_2$C$_2$H$_4$), 2.77 (m, br, 4H, CH$_2$N), 3.04 (m, 4H, CF$_2$CH$_2$CF$_2$), 3.60 (s, 9H, OCH$_3$), 4.31 (m, 4H, CH$_2$OOC).

13C NMR (MeOH-d4): 7.4 (s, CH$_2$Si), 14.6 (s, CH$_2$CH$_2$Si), 18.7 (s, CH$_3$), 21.4 (m, CF$_2$CH$_2$CH$_2$), 33.4 (m, CH$_2$COO), 37.7 (m, CH$_2$CF$_2$CH$_2$), 50.3 (s, NCH$_2$), 57.5 (s, NCH$_2$ CH$_2$COO), 58.9 (m, CF$_2$CH$_2$CF$_2$), 59.4 (s, OCH$_2$), 61.5 (s, CH$_2$OOC), 115.5, 117.5, 119.9, 124.1 (4×m, C$_2$F$_9$), 173.7 (s, COO).

Example 19

Tertiary Amine Fluorosilane from C$_6$ VDF Acrylate

A bis-fluoroalkyl (twin-tail) silane with ester and tertiary amine tether moieties was synthesized according to:

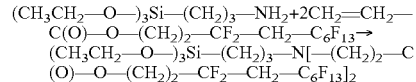

A solution of one equivalent of APTES (Aminopropyl triethoxysilane, CAS#919-30-2) and two equivalents acrylic acid 3,3,5,5,6,6,7,7,8,8,9,9,10,10,10-pentdecafluoro-decyl ester (synthesized according to U.S. Pat. No. 3,916,009, CIBA-GEIGY AG, 1975) in absolute ethanol were allowed to stir at 60° C. for 5 h. The solvent was distilled of under reduced pressure to provide the desired twin-tail silane (tertiary amine fluorosilane) quantitatively as a colorless oil.

1H NMR (MeOH-d4): 0.60 (m, 2H, CH$_2$Si), 1.18 (t, 9H, CH$_3$), 1.56 (m, 2H, CH$_2$CH$_2$Si), 2.47 (m, br, 10H, CF$_2$CH$_2$CH$_2$ and OOCCH2 and NCH$_2$C$_2$H$_4$), 2.77 (m, br, 4H, CH$_2$N), 3.04 (m, 4H, CF$_2$CH$_2$CF$_2$), 3.60 (s, 9H, OCH$_2$), 4.31 (m, 4H, CH$_2$OOC).

13C NMR (MeOH-d4): 7.4 (s, CH$_2$Si), 14.6 (s, CH$_2$CH$_2$Si), 18.7 (s, CH$_3$), 21.4 (m, CF$_2$CH$_2$CH$_2$), 33.4 (m, CH$_2$COO), 37.7 (m, CH$_2$CF$_2$CH$_2$), 50.3 (s, CH$_2$N), 57.6 (OOCCH$_2$CH$_2$N), 58.9 (m, CF$_2$CH$_2$CF$_2$), 59.4 (s, OCH$_2$), 61.5 (s, CH$_2$OOC), 109-124.1 (6×m, C$_2$F$_9$), 173.7 (s, COO).

Example 20

Tertiary Amine Fluorosilane (from C4,2 VDF Acrylate; Michael Addition)

A bis-fluoroalkyl (twin-tail) silane with ester and tertiary amine tether moieties was synthesized according to:

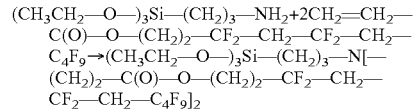

A solution of one equivalent of APTES (Aminopropyl triethoxysilane, CAS#919-30-2) and two equivalents acrylic acid 3,3,5,5,7,7,8,8,9,9,10,10,10-tridecafluoro-decyl ester (synthesized according to U.S. Pat. No. 3,916,009, CIBA-GEIGY AG, 1975) in absolute ethanol were allowed to stir at 60° C. for 5 h. The solvent was distilled of under reduced pressure to provide the desired twin-tail silane (tertiary amine fluorosilane) quantitatively as a colorless oil.

1H NMR (MeOH-d4): 0.58 (m, 2H, $CH_2Si$), 1.20 (t, 9H, $CH_3$), 1.54 (m, 2H, $CH_2CH_2Si$), 2.38 and 2.47 (2×m, 10H, $CF_2CH_2CH_2$ and $OOCCH2$ and $NCH_2C_2H_4$), 2.77 (m, br, 4H, $CH_2N$), 2.85 (m, 4H, $C_4F_9CH_2$), 3.04 (m, 4H, $CF_2CH_2CF_2$), 3.60 (s, 9H, $OCH_2$), 4.30 (m, 4H, $CH_2OOC$).

$^{13}C$ NMR (MeOH-d4): 8.6 (s, $CH_2Si$), 14.6 (s, $CH_2CH_2Si$), 18.7 (s, $CH_3$), 21.4 (m, $CF_2CH_2CH_2$), 33.4 (m, $CH_2COO$), 37.7 (m, $CH_2CF_2CH_2$), 44.3 (m, $C_4F_9CH_2CF2$), 50.3 (m, $CH_2N$), 56.5 (m, $CF_2CH_2CF_2$), 57.5 (s, $NCH_2CH_2COO$), 59.1 (m, $CF_2CH_2CF_2$), 59.5 (s, $OCH_2$), 61.5 (s, $CH_2OOC$), 115.5, 117.5, 119.9, 124.1 (4×m, $C_2F_9$), 173.9 (s, COO).

Example 21

Tertiary Amine Fluorosilane (from PPVE Acrylate; Michael Addition)

A bis-fluoroalkyl (twin-tail) silane with ester and tertiary amine tether moieties was synthesized according to:

$(CH_3CH_2—O—)_3Si—(CH_2)_3—NH_2+2CH_2═CH_2—$
$C(O)—O—(CH_2)_2—C_2F_4—O—C_3F_7 →$
$(CH_3CH_2—O—)_3Si—(CH_2)_3—N[—(CH_2)_2—C$
$(O)—O—(CH_2)_2—C_2F_4—O—C_3F_7]_2$

Acrylic acid was esterified with 2-[2-(heptafluoropropoxy)-tetrafluoroethyl]-ethyl alcohol (US 2008113199 A1) in the presence catalytic amounts of p-toluene sulfonic acid to yield acrylic acid 3,3,4,4-tetrafluoro-4-heptafluoropropyloxy-butyl ester quantitatively. The ester was washed with water and distilled prior to the reaction with APTES (Aminopropyl triethoxysilane, CAS#919-30-2). A solution of one equivalent of APTES and two equivalents acrylic acid 3,3,4,4-tetrafluoro-4-heptafluoropropyloxy-butyl in absolute ethanol were allowed to stir at 60° C. for 5 h. The solvent was distilled of under reduced pressure to provide the desired twin-tail silane (tertiary amine fluorosilane) quantitatively as a colorless oil.

$^1H$ NMR ($CDCl_3$): 0.58 (m, 2H, $CH_2Si$), 1.21 (t, 9H, $CH_3$), 1.54 (m, 2H, $CH_2CH_2Si$), 2.46 and 2.52 (2×m, 10H, $CF_2CH_2$ and $NCH_2C_2H_4$ and $OOCCH2$), 2.76 (m, 4H, $CH_2N$), 3.62 (m, 6H, $OCH_2$), 4.36 (m, 1H, $CH_2OOC$).

$^{13}C$ NMR (MeOH-d4): 8.6 (s, $CH_2Si$), 14.5 (s, $CH_2CH_2Si$), 18.7 (s, $CH_3$), 21.5 (m, $CF_2CH_2CH_2$), 31.4 (t, $CF_2CH_2$), 50.3 (m, $CH_2N$), 59.1 (s, $NCH_2$), 57.4 ($OOCCH_2CH_2N$), 59.4 (s, $CH2O$), 61.5 (s, $CH_2OOC$), 115.5, 117.5, 119.9, (3×m, CF), 173.6 (s, COO).

Example 22

Synthesis Tertiary Amine from C4-Oxirane

A mixture one equivalent of APTES and two equivalents 2-(2,2,3,3,4,4,5,5,6,6,7,7,7-tridecafluoro-heptyl)-oxirane (Cirkva, V. et al. *J. Fluorine Chem.* 1997, 83, 151-158), dissolved in THF, was allowed to stir at 50° C. for 5 h to provide the desired twin-tail silane quantitatively as a amber oil upon removal of the solvent under reduced pressure.

$^1H$ NMR (THF-d8): 0.69 (m, 2H, $CH_2Si$), 1.29 (m, $CH_3$), 1.56 (m, 2H, $CH_2CH_2Si$), 2.31 (2×m, 4H, $CF_2CH_2$), 2.50-2.80 (m, 6H, $CH_2N$), 3.81 (m, 6H, $OCH_2$), 4.08, 4,15 (2×s, br, 2H, CHOH).

$^{13}C$ NMR ($CDCl_3$): 8.0 (s, $CH_2Si$), 18.6 (s, $CH_2CH_3$), 23.7 (s, $CH_2CH_2Si$), 36.4 (m, $CF_2CH_2$), 52.3 (s, $NCH_2$), 55.1 (s, $CH_2N$), 58.7 (s, $OCH_2$), 63.3 (m, $HOCHCH_2N$), 108, 110, 116, 118 (m, $CF_2$ and $CF_3$).

What is claimed is:

1. A fluorosilane represented by

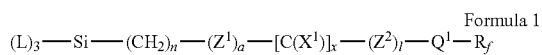

Formula 1 wherein:
each n is independently an integer from 1 to 12;
wherein a=1, x=0; and l=0;
L is independently chosen from a hydrolysable or non-hydrolysable monovalent group
$R_f$ is chosen from a $C_2$-$C_{12}$ perfluoroalkyl;
$Q^1$ is chosen from the group consisting of a $C_2$-$C_{12}$ hydrocarbylene optionally interrupted by at least one divalent organic group;
$X^1$ is chosen from O or S;
a) $Z^1$ is —N[-$Q^3$-($R_f$)]—; and
b) $Q^1$ and $Q^3$ are independently chosen from the group consisting of a $C_2$-$C_{12}$ hydrocarbylene interrupted by at least one of —C(O)—O— or —O—C(O)—, and further interrupted by at least one divalent organic group.

2. The fluorosilane of claim 1 being a tertiary amine fluorosilane wherein:
a=1, x=0; and l=0; and
$Z^1$ is —N[-$Q^3$-($R_f$)]-;
said tertiary amine represented by the formula:

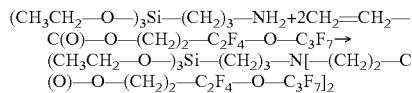

$Q^1$ and $Q^3$ are independently chosen from the group consisting of a $C_2$-$C_{12}$ hydrocarbylene interrupted by at least one —C(O)—O— and optionally further interrupted by at least one divalent moiety chosen from the group consisting of —S—, —S(O)—, —S(O)$_2$—, —N($R^1$)—C(O)—, —C(O)—N($R^1$)—, —($R^1$)N—S(O)$_2$—, and

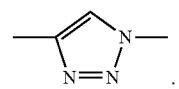

3. A fluorosilane represented by

Formula 1 wherein:
each n is independently an integer from 1 to 12;
wherein a=1, x=0; and l=0;
  L is independently chosen from a hydrolysable or non-hydrolysable monovalent group;
  $R_f$ is chosen from a $C_2$-$C_{12}$ perfluoroalkyl provided that: i) one fluorine atom of the perfluoroalkyl can be replaced by hydrogen, and/or ii) the perfluoroalkyl can be interrupted by at least one oxygen, methylene, or ethylene;
  $Q^1$ is chosen from the group consisting of a $C_2$-$C_{12}$ hydrocarbylene optionally interrupted by at least one divalent organic group;
  $X^1$ is chosen from O or S;
  a) $Z^1$ is —N[-$Q^3$-($R_f$)]—; and
  b) $Q^1$ and $Q^3$ are independently chosen from the group consisting of a $C_2$-$C_{12}$ hydrocarbylene interrupted by at least one of —C(O)—O— or —O—C(O)—, and optionally further interrupted by at least one divalent organic group.

4. The fluorosilane of claim 1 being a tertiary amine fluorosilane wherein:
a=1, x=0; and l=0; and
$Z^1$ is —N[-$Q^3$-($R_f$)]—;

said tertiary amine represented by the formula:

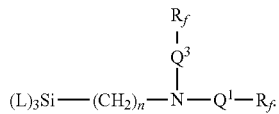

$Q^1$ and $Q^3$ are independently chosen from the group consisting of a $C_2$-$C_{12}$ hydrocarbylene interrupted by at least one —C(O)—O— and optionally further interrupted by at least one divalent moiety chosen from the group consisting of —S—, —S(O)—, —S(O)$_2$—, —N($R^1$)—C(O)—, —C(O)—N($R^1$)—, —($R^1$)N—S(O)$_2$—, and

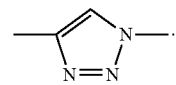

* * * * *